(12) United States Patent
Kaneko

(10) Patent No.: US 8,994,803 B2
(45) Date of Patent: Mar. 31, 2015

(54) IMAGE APPARATUS AND CONTROL METHOD THEREOF CONFIGURED TO DETERMINE OPTICAL PROBE ABNORMALITY

(75) Inventor: Kenji Kaneko, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 46 days.

(21) Appl. No.: 13/216,707

(22) Filed: Aug. 24, 2011

(65) Prior Publication Data

US 2012/0007974 A1      Jan. 12, 2012

Related U.S. Application Data

(63) Continuation of application No. PCT/JP2010/000523, filed on Jan. 29, 2010.

(30) Foreign Application Priority Data

Feb. 24, 2009 (JP) ................................. 2009-041244

(51) Int. Cl.
*A61B 1/04* (2006.01)
*G01N 21/47* (2006.01)
(Continued)

(52) U.S. Cl.
CPC .......... *G01N 21/4795* (2013.01); *A61B 5/0066* (2013.01); *A61B 5/0084* (2013.01); *A61B 5/02007* (2013.01); *A61B 5/6852* (2013.01)
USPC ........................................................ 348/68

(58) Field of Classification Search
CPC ........................................... H04N 2005/2255
USPC ........................................................ 348/68
See application file for complete search history.

(56) References Cited

U.S. PATENT DOCUMENTS 6,327,493 B1    12/2001   Ozawa et al.
2003/0004412 A1   1/2003   Izatt et al.
(Continued)

FOREIGN PATENT DOCUMENTS

EP   2 062 526 A1   5/2009
JP   11-337477 A   12/1999
(Continued)

OTHER PUBLICATIONS

International Search Report (PCT/ISA/210) issued on Mar. 16, 2010, by Japanese Patent Office as the International Searching Authority for International Application No. PCT/JP2010/000523.
(Continued)

*Primary Examiner* — Dave Czekaj
*Assistant Examiner* — James Pontius
(74) *Attorney, Agent, or Firm* — Buchanan Ingersoll & Rooney PC

(57) ABSTRACT

An imaging apparatus generates a cross-sectional image in the longitudinal direction inside a body cavity (e.g., blood vessel) by using an interference signal. The apparatus includes an obtaining unit for obtaining line data, and a judgment unit for judging whether or not the optical probe unit operates in a normal state based on existence or non-existence of intensity change in at least a portion of signals within the obtained line date, based on existence or non-existence of change of position in the depth direction in which the portion of signals appear, or based on change quantity per unit time with respect to the position in the depth direction in which the portion in the depth direction of signals appear.

7 Claims, 10 Drawing Sheets

(51) Int. Cl.
*A61B 5/00* (2006.01)
*A61B 5/02* (2006.01)

(56) References Cited

U.S. PATENT DOCUMENTS

| | | | |
|---|---|---|---|
| 2004/0120027 A1* | 6/2004 | Kosaka | 359/341.1 |
| 2004/0181148 A1* | 9/2004 | Uchiyama et al. | 600/425 |
| 2005/0168751 A1* | 8/2005 | Horii et al. | 356/479 |
| 2006/0058622 A1 | 3/2006 | Tearney et al. | |
| 2009/0073455 A1 | 3/2009 | Onimura | |
| 2009/0213387 A1 | 8/2009 | Nakabayashi et al. | |
| 2010/0130872 A1 | 5/2010 | Irisawa | |

FOREIGN PATENT DOCUMENTS

| | | | | |
|---|---|---|---|---|
| JP | 2000-097846 A | 4/2000 | | |
| JP | 2001-079007 A | 3/2001 | | |
| JP | 2004-223269 A | 8/2004 | | |
| JP | 2006-015134 A | 1/2006 | | |
| JP | 2008-014914 | * | 1/2008 | G01N 21/17 |
| JP | 2008-014914 A | 1/2008 | | |
| JP | 2008-510586 A | 4/2008 | | |
| JP | 2009-014751 A | 1/2009 | | |
| JP | 2009-066014 A | 4/2009 | | |
| WO | 2006/024015 A1 | 3/2006 | | |
| WO | WO 2008/044539 A1 | 4/2008 | | |
| WO | WO 2009/004953 A1 | 1/2009 | | |

OTHER PUBLICATIONS

Extended European Search Report issued Feb. 11, 2013 by the European Patent Office in European Application No. 10745903 (8 pages).

* cited by examiner

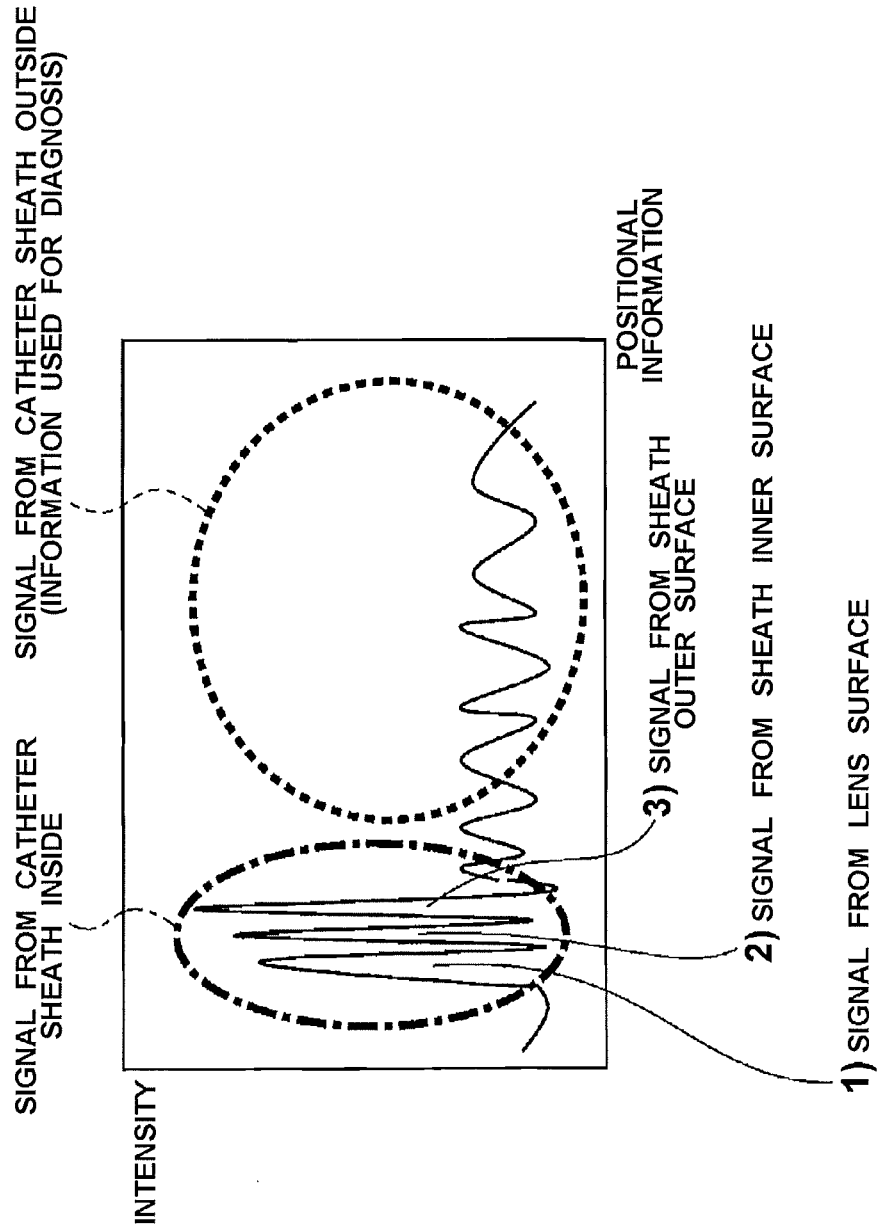

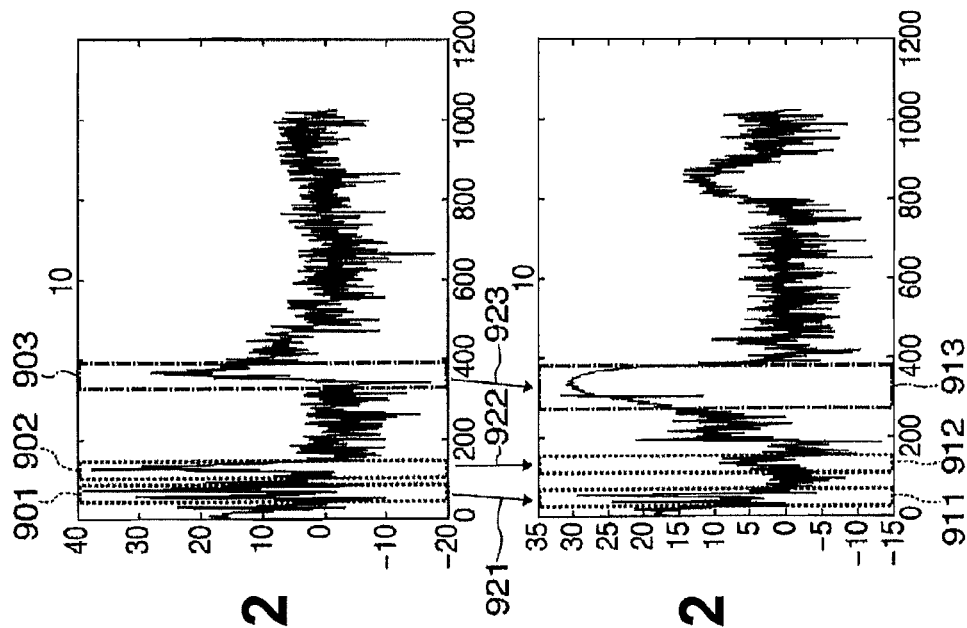
FIG.9A-2      FIG.9B-2
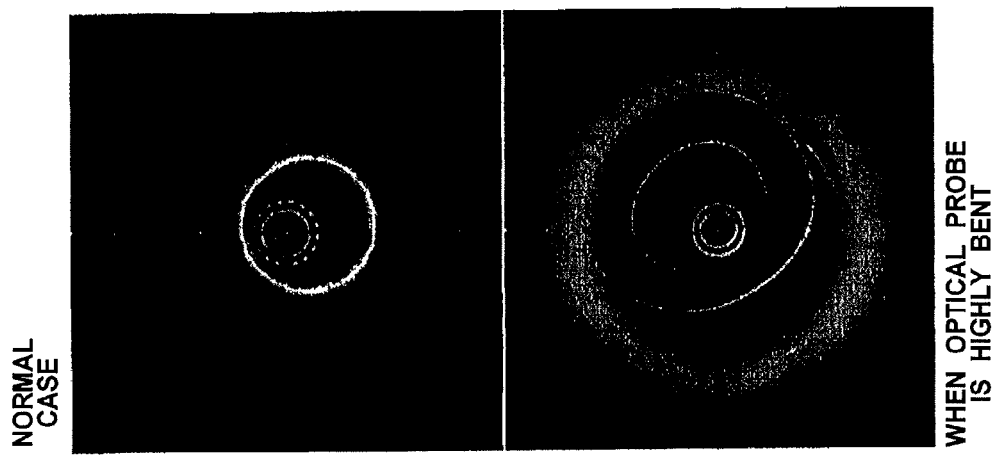
FIG.9A-1 NORMAL CASE
FIG.9B-1 WHEN OPTICAL PROBE IS HIGHLY BENT

US 8,994,803 B2

IMAGE APPARATUS AND CONTROL METHOD THEREOF CONFIGURED TO DETERMINE OPTICAL PROBE ABNORMALITY

This application is a continuation of International Application No. PCT/JP2010/000523 filed on Jan. 29, 2010, and claims priority to Japanese Application No. 2009-041244 filed on Feb. 24, 2009, the entire content of both of which is incorporated herein by reference.

TECHNOLOGICAL FIELD

The present invention relates to an imaging apparatus and a control method for controlling such an apparatus.

BACKGROUND DISCUSSION

An optical coherence tomography (OCT) apparatus has been used for a diagnosis of arteriosclerosis, for a diagnosis before operation at the time of an endovascular treatment by a high functional catheter such as a balloon catheter, a stent and the like, or for confirming results after an operation.

The optical coherence tomography apparatus is an apparatus having at its distal end an optical probe unit which is built-in with a transmitting and receiving unit mounted with an optical lens and an optical mirror, and an optical fiber inside the blood vessel. The probe is insertable into a blood vessel whereby measurement light is emitted to the blood vessel while rotating the transmitting and receiving unit. A radial scan is carried out by receiving reflected light from a biological tissue, and a cross-sectional image of the blood vessel based on interference signal is visualized by making the reflected light obtained depending on this radial scan and a reference light split from the measurement light beforehand interfere each other. An example of this optical coherence tomography apparatus is disclosed in Japanese Unexamined Patent Publication No. 2001-79007.

Recently, as an enhancement of the optical coherent tomography apparatus, an optical frequency domain imaging (OFDI) apparatus has been developed which utilizes wavelength swept light source.

With respect to the optical frequency domain imaging (OFDI) apparatus utilizing wavelength swept light source, the basic construction of the apparatus is similar to that of the optical coherence tomography (OCT) apparatus, but one difference is that a light source having a longer wavelength compared with the optical coherent tomography apparatus is used and also, light having different wavelengths is emitted continuously. Then, mechanism for variably changing the optical path length of the reference light is made unnecessary by employing a construction in which reflected-light intensity at each point in the depth direction of the biological tissue is determined by frequency analysis of the interference signal.

The description which follows refers to "imaging apparatus" which is intended to be a generic term that includes both the optical coherence tomography (OCT) apparatus and the optical frequency domain imaging (OFDI) apparatus utilizing wavelength swept light source.

Generally, on an occasion when carrying out a radial operation of a transmitting and receiving unit in order to visualize a cross-sectional image by using such an imaging apparatus, it is desirable to be minimally invasive with respect to a patient.

On the other hand, during the radial operation of the transmitting and receiving unit, occurrence of various kinds of troubles in an optical probe unit can occur such that an injury is exerted to a blood vessel of a patient. For example, in a case in which the catheter is bent extremely or in a case in which it is trapped by a stent or the like, rotation torque for rotating the transmitting and receiving unit cannot be transmitted to the transmitting and receiving unit and it takes on a state in which the optical fiber will coil on itself at the proximal side. In this case, a pulling force is added to the catheter and it happens that the catheter is damaged or bent inside the blood vessel, so that there is a possibility that injury is exerted with respect to the blood vessel.

Also, in case of carrying out pull-back in a state in which the transmitting and receiving unit and the catheter are stacked at the bent portion, at the stent or the like, similarly, a pulling force is added with respect to the catheter, it happens that the catheter can be damaged or bent inside the blood vessel, so that there is a possibility that injury is exerted with respect to the blood vessel.

SUMMARY OF THE INVENTION

An imaging apparatus disclosed here by way of example includes an optical probe unit positionable in a body cavity and having a transmitting and receiving unit which carries out transmission and reception of light continuously, with reflected light from the body cavity is obtained at the transmitting and receiving unit during rotational movement of the transmitting and receiving unit and longitudinal movement inside the body cavity so that a cross-sectional image in the longitudinal direction of the body cavity is generated based on interference signal generated by the obtained reflected light. The apparatus also includes an obtaining unit for obtaining signals which indicate intensity distribution of the interference signal from the transmitting and receiving position of the light to a certain depth position inside the body cavity, which are generated every time when the transmitting and receiving unit carries out transmission and reception of light, and a judgment unit for judging whether or not the optical probe unit is normal based on existence or non-existence of intensity change in at least a portion of signals obtained by the obtaining unit, based on existence or non-existence of change of position in the depth direction in which the portion of signals appear, or based on change quantity per unit time with respect to the position in which the portion of signals appear.

Also disclosed here is a control method in an imaging apparatus comprised of an optical probe unit positionable in a body cavity and comprising a transmitting and receiving unit which carries out transmission and reception of light continuously, with reflected light from the body cavity being received at the transmitting and receiving unit during rotational and longitudinal movement of the transmitting and receiving unit inside the body cavity so that a cross-sectional image in a longitudinal direction of the body cavity is generated based on interference signal generated by the received reflected light. The method comprises obtaining signals generated when the transmitting and receiving unit carries out transmission and reception of light and which indicate intensity distribution of interference signal from the transmitting and receiving position of the light to a certain depth position inside the body cavity, and judging whether or not the optical probe unit is normal based on the existence or non-existence of intensity change in at least a portion of signals obtained in the obtaining process, based on existence or non-existence of change of position in the depth direction in which the portion of signals appear, or based on change quantity per unit time with respect to the position in the depth direction in which the portion of signals appear.

According to another aspect, an imaging apparatus comprises an optical probe unit positionable in a body cavity and comprising a transmitting and receiving unit configured to transmit light and to receive reflected light which has reflected from within the body cavity as the transmitting and receiving unit rotates and moves longitudinally in the body cavity, with a cross-sectional image of the body cavity being generated based on an interference signal generated using the received reflected light, the transmitting and receiving unit being positioned in a catheter sheath; an obtaining unit which obtains signals indicating an intensity distribution of the interference signal from a transmitting and receiving position of the light to a depth position inside the body cavity; and determining means for determining that the optical probe unit is abnormal: i) when there exists a change in the intensity of at least a portion of the signals acquired by the obtaining unit; ii) when there exists a change of position in a depth direction in which the portion of signals appear; or iii) based on change quantity per unit time with respect to the position in which the portion of signals appear.

The apparatus and method make it possible to visualize a cross-sectional image more safely by detecting abnormality which occurs at the optical probe unit in the imaging apparatus.

On an occasion of the radial operation of the transmitting and receiving unit, it is possible to monitor the occurrence of trouble in such an optical probe unit and to take action in a desirable manner in a case in which a trouble occurs. The apparatus and method here are thus better able to detect a potentially trouble-creating situation without significant delay so that a cause of the trouble can be determined.

BRIEF DESCRIPTION OF THE DRAWINGS

Additional details, features and aspects of the apparatus and method disclosed here will become more apparent from the detailed description below considered with reference to the accompanying drawing figures which describe and illustrate, by way of example, embodiments of the apparatus and method disclosed here. In the drawing figures, like features or elements are designated by like reference numerals.

FIG. 8 is a diagram showing one example of line data used for generation of a cross-sectional image.

FIGS. 9A-1, 9A-2, 9B-1 and 9B-2 are diagrams showing one example of line data of a normal case, line data of an abnormal case, and cross-sectional images corresponding to the respective ones thereof.

DETAILED DESCRIPTION

[First Embodiment]
1. Outward Appearance and Construction of Imaging Apparatus

Figure 1:
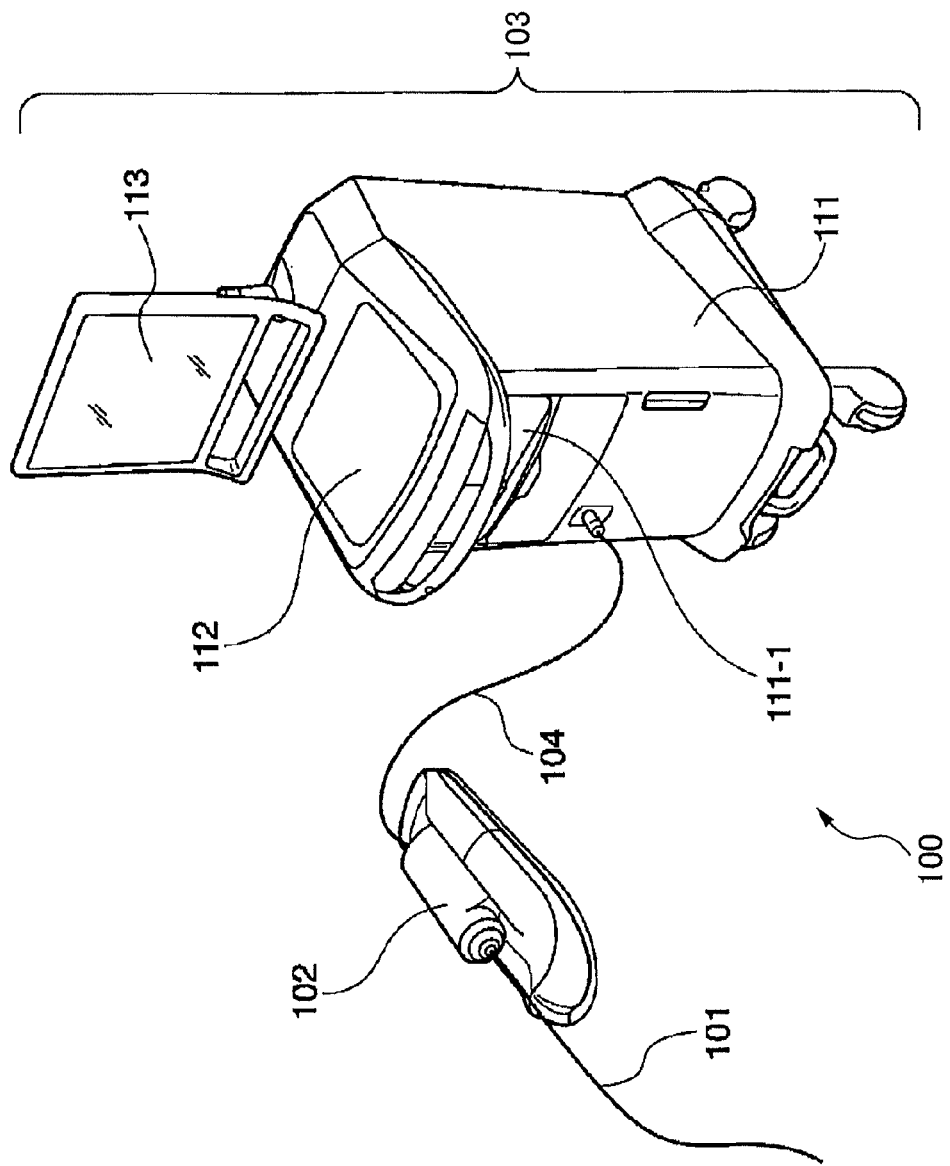
FIG. 1 is a perspective view of an outward appearance and construction of an imaging apparatus.

FIG. 1 illustrates an imaging apparatus (optical coherent tomography apparatus or optical frequency domain imaging apparatus utilizing wavelength swept light source) 100 according to one embodiment disclosed by way of example. As shown in FIG. 1, the imaging apparatus 100 includes an optical probe unit 101, a scanner & pull-back unit 102 and a steering control apparatus 103. The scanner & pull-back unit 102 and the steering control apparatus 103 are connected by a signal wire 104.

In use, the optical probe unit 101 is inserted directly into a blood vessel and a state inside the blood vessel is determined or measured by using an imaging core 504. The scanner & pull-back unit 102 is removable or detachable with respect to the optical probe unit 101 in which a motor is built-in, and provides radial operation of the transmitting and receiving unit 503 inside the optical probe unit 101 according to the driving operation of an installed motor.

The steering control apparatus 103 is operable for inputting various kinds of setting values, for example when carrying out intravascular optical coherence tomographic diagnosis, and also processes data obtained by the measurement for display as a cross-sectional image(s).

The steering control apparatus 103 includes a main body control unit 111 which, for example, processes data obtained by measurement and outputs the processed result. A printer & DVD recorder 111-1 prints the process result of the main body control unit 111, stores it as data.

An operational panel 112 allows a user to input various kinds of setting values, and a display apparatus 113, which may be in the form of an LCD monitor, displays the process result in the main body control unit 111.

2. Features and Operational Aspects of Optical Coherence Tomography Apparatus

Figure 2:
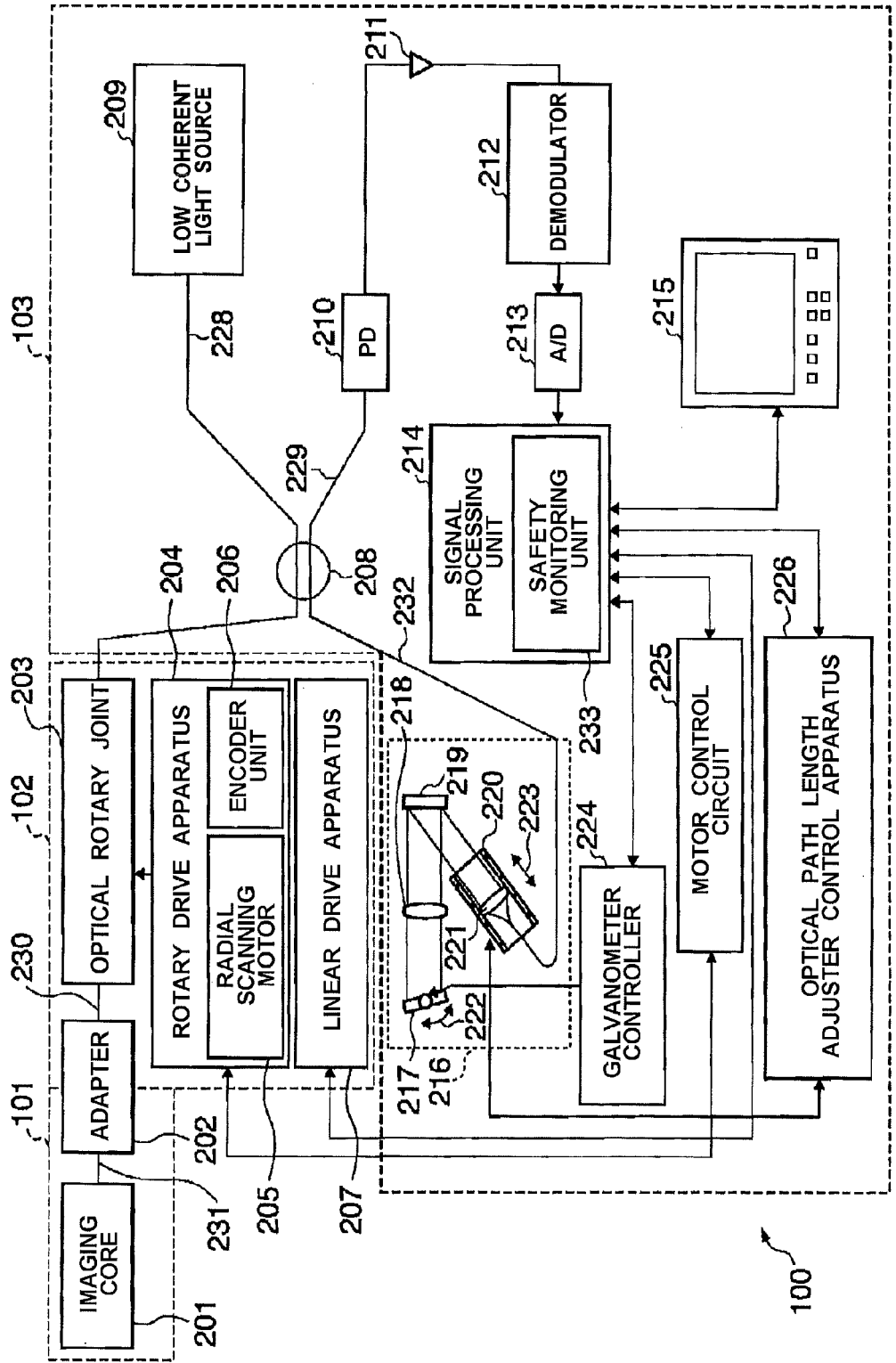
FIG. 2 is a schematic illustration of the construction of an optical coherence tomography apparatus.

As a part of the imaging apparatus 100 according to this embodiment, FIG. 2 illustrates various features and aspects of the optical coherence tomography apparatus. A low coherent light source 209, such as a superluminescent diode or the like, outputs a low coherent light whose wavelength is around 1310 nm and which shows coherence only in such a short distance range that the coherence length is around several μm to ten and several μm.

Consequently, when splitting this light into two lights and thereafter, again mixing them, it is detected as interference signal in a case in which difference of the two optical path lengths from the split point to the mixed point is within a short distance range of around several μm to ten and several μm, and in a case in which the difference of the optical path lengths is longer than that, it is not detected as an interference signal.

The light of the low coherent light source 209 enters one end of a first single mode fiber 228 and is transmitted to the distal end of the fiber. The first single mode fiber 228 is coupled with second single mode fiber 229 and third single mode fiber 232 optically by an optical coupling unit 208.

The optical coupling unit refers to an optical component which can split one optical signal into two or more outputs, which can couple two or more inputted optical signals into one output and the like, and it is possible for the light of the low coherent light source 209 to be transmitted by being split into a maximum of three optical paths depending on the aforesaid optical coupling unit 208.

The scanner & pull-back unit 102 is provided on the distal end side from the optical coupling unit 208 of the first single mode fiber 228. The inside of the scanner & pull-back unit 102 is provided with an optical rotary joint 203 which couples between a non-rotation unit and a rotation unit, and which transmits light.

Further, the distal end side of a fourth single mode fiber 230 inside the optical rotary joint 203 is connected in a freely detachable manner with a fifth single mode fiber 231 of the optical probe unit 101 through an adaptor 202. Thus, the light from the low coherent light source 209 is transmitted to the fifth single mode fiber 231 which is inserted into the inside of the imaging core 201 which repeatedly transmits and receives the light and which is rotationally driven.

The light transmitted to the fifth single mode fiber 231 is illuminated with respect to the biological tissue inside the blood vessel from the distal end of the imaging core 201 while being scanned radially. Then, a portion of the reflected light scattered on the surface or inside of the biological tissue is taken-in or received by the imaging core 201 and returns to the first single mode fiber 228 side by way of the opposite optical path, and a portion thereof moves to the second single mode fiber 229 side by the optical coupling unit 208. Then, the portion emanates from one end of the second single mode fiber 229 and light-received by a photo detector (for example, photodiode 210).

The rotation unit side of the optical rotary joint 203 is driven rotationally by a radial scanning motor 205 of a rotary drive apparatus 204. Also, the rotary angle of the radial scanning motor 205 is detected by an encoder unit 206. Further, the scanner/pull-back unit 102 is provided with a linear drive apparatus 207 and defines movement (longitudinal or axial motion) in the longitudinal direction (distal direction inside the body cavity and the opposite direction) of the imaging core 201 based on instruction or input from a signal processing unit 214. The axial motion is realized by a fact that the linear drive apparatus 207 moves a scanner including the optical rotary joint 203 based on a control signal from the signal processing unit 214.

At that time, by moving only the imaging core 201 housed inside the catheter sheath in the axial direction while maintaining the catheter sheath of the optical probe unit 101 fixed inside the blood vessel, the axial motion is carried out without injuring the blood vessel wall.

A variable mechanism of optical path length 216 for changing the optical path length of the reference light is provided on the distal end side (reference light path) from the optical coupling unit 208 of the second single mode fiber 229, with a variable mechanism of optical path length 216 for changing the optical path length of the reference light.

This variable mechanism of optical path length 216 is provided with a first optical path length changing unit for changing, in a relatively high speed manner, the optical path length corresponding to an inspection range in the depth direction (emission direction of measurement light) of the biological tissue and a second optical path length changing unit for changing the optical path length corresponding to fluctuation of the length thereof so as to be able to absorb fluctuation of the length of the individual optical probe unit 101 in the event the optical probe unit 101 is exchanged.

There is arranged a grating 219, which is facing the distal end of the second single mode fiber 229 through a collimating lens 221 which is mounted on an one-axis stage 220 together with this distal end and is freely movable in the direction shown by an arrow 223. Also, there is mounted a minute angle rotatable galvanometer 217 as a first optical path length changing unit through this grating 219 (diffraction grating) and a corresponding lens 218. This galvanometer 217 is rotated in a relatively high-speed manner in the direction of the arrow 222 under the control of a galvanometer controller 224.

The galvanometer 217 is a meter which reflects the light by a mirror of the galvanometer and is constructed so as to rotate the minor mounted on a movable portion in a relatively high-speed manner by applying an alternating-current drive signal to the galvanometer which functions as a reference mirror.

More specifically, a drive signal is applied with respect to the galvanometer 217 from the galvanometer controller 224, and by rotating high-speedily in the arrow 222 direction caused by the drive signal, the optical path length of the reference light changes in a relatively high-speed manner as much as the optical path length corresponding to an inspection range in the depth direction of the biological tissue. One cycle of this change of the optical path difference becomes a period for obtaining the interference signal for one line.

On the other hand, in case of exchanging the optical probe unit 101, the one-axis stage 220 functions as a second optical path length changing unit having as much as a variable range of the optical path length, which can absorb the fluctuation of the optical path length of the optical probe unit 101. The one-axis stage 220 is also able to operate as an adjuster for adjusting an offset. For example, even in a case in which the distal end of the optical probe unit 101 is not closely-attached to the surface of the biological tissue, it becomes possible, by minutely changing the optical path length depending on the one-axis stage 220, to set a state of interfering with the reflected light from the surface position of the biological tissue.

The light whose optical path length is changed by the variable mechanism of optical path length 216 is combined with the light obtained from the first single mode fiber 228 side by the optical coupling unit 208 provided on the way of the second single mode fiber 229 and is detected by a photodiode 210 as an interference signal.

The interference signal received by the photodiode 210 in this manner is photoelectrically converted and is amplified by an amplifier 211.

Thereafter, it is inputted to a demodulator 212 and in the demodulator 212, a demodulation process for extracting only a signal component of the interfered light is performed, and an output thereof is inputted to an A/D converter 213.

In the A/D converter 213, the interference signal is applied with sampling, for example, for 200 points and the digital data of one line ("interference signal data") is generated. In this case, the sampling frequency is a value obtained by dividing one scan time period of the optical path length by 200.

The interference signal data of one line unit which is generated in the A/D converter 213 is inputted to a signal processing unit 214. In the signal processing unit 214, by converting the interference signal data in the depth direction of the biological tissue to a video signal, cross-sectional images at respective positions inside the blood vessel are formed, and are outputted to a LCD monitor 215 (corresponding to reference number 113 of FIG. 1) by a predetermined frame rate.

The signal processing unit 214 is connected further with an optical path length adjuster control apparatus 226. The signal processing unit 214 carries out position control of the one-axis stage 220 through the optical path length adjuster control apparatus 226. Also, the signal processing unit 214 is connected with a motor control circuit 225 and controls the rotary drive of the radial scanning motor 205.

Also, the signal processing unit 214 is connected with a galvanometer controller 224 for controlling scan of the optical path length of a reference mirror (galvanometer minor) and the galvanometer controller 224 outputs a drive signal to the signal processing unit 214. The motor control circuit 225 is synchronized with the galvanometer controller 224 by using this drive signal.

Further, the signal processing unit 214 is provided with a monitoring unit 233 (safety monitoring unit) and detects occurrence of abnormality in the optical probe unit 101 based on the line data, and if required, an alarm is outputted to the LCD monitor 215.

Figure 3:
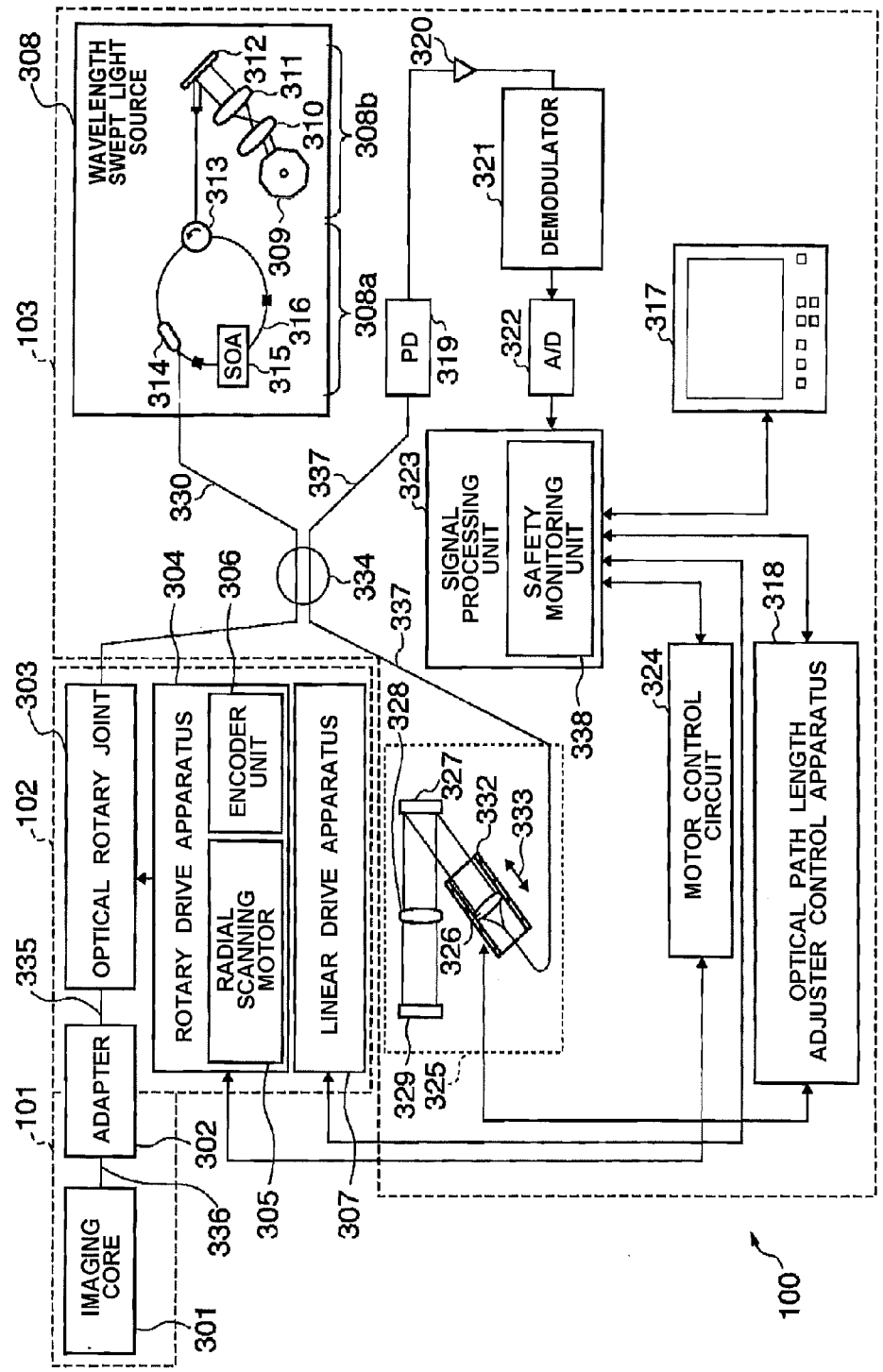
FIG. 3 is a schematic illustration of the construction of an optical frequency domain imaging apparatus utilizing wavelength swept light source.

3. Features and Operational Aspects of Optical Frequency Domain Imaging Apparatus Utilizing Wavelength Swept Light Source As a part of the imaging apparatus 100 disclosed here by way of example, and with reference to FIG. 3, the following description is provided about operational or functional aspects of the optical frequency domain imaging apparatus utilizing wavelength swept light source. FIG. 3 illustrates functional or operational aspects of the optical frequency domain imaging apparatus utilizing wavelength swept light source 100. The description below will primarily discuss differences relative to the optical coherence tomography apparatus described above with reference to FIG. 2.

The apparatus includes a wavelength swept light source 308 in which is used a wavelength swept laser. The wavelength swept light source 308 using the swept laser is one kind of an extended-cavity laser which is composed of an optical fiber 316 coupled with an SOA 315 (semiconductor optical amplifier) in a ring shape and a polygon scanning filter (308b).

The light outputted from the SOA 315 advances inside the optical fiber 316 and enters into the polygon scanning filter 308b, and the light of which wavelength is selected here is amplified by the SOA 315 and finally is outputted from a coupler 314.

In the polygon scanning filter 308b, the wavelength is selected by using the combination of a diffraction grating 312 for dispersing the light and a polygonal minor 309. Specifically, the light dispersed by the diffraction grating 312 is focused on the surface of the polygonal mirror 309 by two pieces of lens (310, 311). Thus, only the light having wavelength, which is perpendicular to the polygonal minor 309 returns to the same optical path and is outputted from the polygon scanning filter 308b, so that by rotating the polygonal minor 309, it is possible to carry out time sweep of the wavelength.

With respect to the polygonal minor 309, for example, a mirror having thirty-two facets is used and a rotational speed thereof is around 50000 rpm. Depending on a unique wavelength sweep system in which the polygonal mirror 309 and the diffraction grating 312 are combined, it is possible to employ wavelength sweep of a relatively high speed and a relatively high power output.

The light of the wavelength swept light source 308 which is outputted from the coupler 314 enters into one end of a first single mode fiber 330 and is transmitted to the distal end side. The first single mode fiber 330 is coupled optically with a second single mode fiber 337 and a third single mode fiber 331 in an optical coupling unit 334. Therefore, it is possible for the light entering into the first single mode fiber 330 to be transmitted by being split into a maximum of three optical paths by this optical coupling unit 334.

On the distal end side from the optical coupling unit 334 of the first single mode fiber 330 there is provided an optical rotary joint 303 which couples between a non-rotation unit and a rotation unit and which transmits the light.

Further, the distal end side of a fourth single mode fiber 335 inside the optical rotary joint 303 is connected freely detachably with a fifth single mode fiber 336 of the optical probe unit 101 through an adaptor 302. Thus, the light from the wavelength swept light source 308 is transmitted to the fifth single mode fiber 336 which is inserted into the imaging core 301 and which is rotationally drivable.

The transmitted light is illuminated while being radially scanned from the distal end side of the imaging core 301 with respect to the biological tissue from inside of the body cavity. Then, a portion of the reflected light scattered at the surface or inside of the biological tissue is taken-in or received by the imaging core 301 and returns to the first single mode fiber 330 side by way of the opposite optical path. Further, a portion thereof is moved to the second single mode fiber 337 side by the optical coupling unit 334, is transmitted from one end of the second single mode fiber 337, and is light-received by a photo detector (for example, photodiode 319).

The rotation unit side of the optical rotary joint 303 is driven rotationally by a radial scanning motor 305 of a rotary drive apparatus 304. Also, the rotary angle of the radial scanning motor 305 is detected by an encoder unit 306. Further, the scanner & pull-back unit 102 includes a linear drive apparatus 307 which defines or provides axial movement of the imaging core 301 based on an instruction from a signal processing unit 323.

On the other hand, there is provided, on the distal end side from the optical coupling unit 334 of the second single mode fiber 337, with a variable mechanism of optical path length 325 for fine-adjusting the optical path length of the reference light.

This variable mechanism of optical path length 325 is provided with an optical path length changing unit for changing the optical path length corresponding to the length of fluctuation thereof so as to be able to absorb fluctuation of the length of the individual optical probe unit 101 in case of using the optical probe unit 101 by being exchanged.

The third single mode fiber 331 and a collimating lens 326 are provided on a freely movable one-axis stage 332 as shown by an arrow 333 in the optical axis direction thereof, and they form the optical path length changing unit.

Specifically, the one-axis stage 332 functions as the optical path length changing unit having as much as variable range of the optical path length so as to absorb fluctuation of the optical path length of the optical probe unit 101 in case the optical probe unit 101 is exchanged. Further, the one-axis stage 332 is provided with also a function as an adjuster for adjusting an offset. For example, in a case in which the distal end of the optical probe unit 101 is not closely-attached to the surface of the biological tissue, it is possible, by minute-changing the optical path length depending on the one-axis stage, to set a state of interfering with the reflected light from the surface position of the biological tissue.

The light whose optical path length is fine-adjusted by the variable mechanism of optical path length 325 is combined with the light obtained from the first single mode fiber 330 side by the optical coupling unit 334 provided on the way to the third single mode fiber 331 and is detected by the photodiode 319 as an interference signal.

A interference signal received by the photodiode 319 in this manner is converted photoelectrically, is amplified by an amplifier 320 and thereafter, is inputted to a demodulator 321. In this demodulator 321, a demodulation process for extracting only a signal component of the interfering light is performed and an output thereof is inputted to an A/D converter 322 as an interferogram.

In the A/D converter 322, the interferogram is applied with sampling, for example, by 180 MHz for 2048 points, and digital data (interference signal data) of one line is generated. A reason why a sampling frequency of 180 MHz is mentioned as an example is because it is assumed that digital data of 2048 points corresponding to about 90% of the period of wavelength sweep (12.5 μsec) is extracted when the repetition frequency of wavelength sweep is set to 80 kHz. The method and apparatus disclosed here are not limited in this regard.

The interference signal data of one line unit, which is generated in the A/D converter 322, is inputted to the signal processing unit 323. In the signal processing unit 323, the interference signal data are frequency-resolved by FFT (Fast Fourier Transform) and data in the depth direction are generated, and by coordinate-converting this data, cross-sectional images at respective positions inside the blood vessel are formed and outputted to an LCD monitor 317 (corresponding to reference numeral 113 of FIG. 1) at a predetermined frame rate.

The signal processing unit 323 is connected further with an optical path length adjuster control apparatus 318. The signal processing unit 323 carries out control of the position of the one-axis stage 332 through the optical path length adjuster control apparatus 318. Also, the signal processing unit 323 is connected with a motor control circuit 324 and receives a video synchronization signal of the motor control circuit 324. In the signal processing unit 323, formation of the cross-sectional image is carried out in synchronization with the received video synchronization signal.

Also, the video synchronization signal of this motor control circuit 324 is transmitted also to the rotary drive apparatus 304, and the rotary drive apparatus 304 outputs a drive signal in synchronization with the video synchronization signal. Further, the signal processing unit 323 is provided with a safety monitoring unit 338 and detects the occurrence of abnormality in the optical probe unit 101 based on the line data, and if required, an alarm is outputted to the LCD monitor 317.

Figure 4:
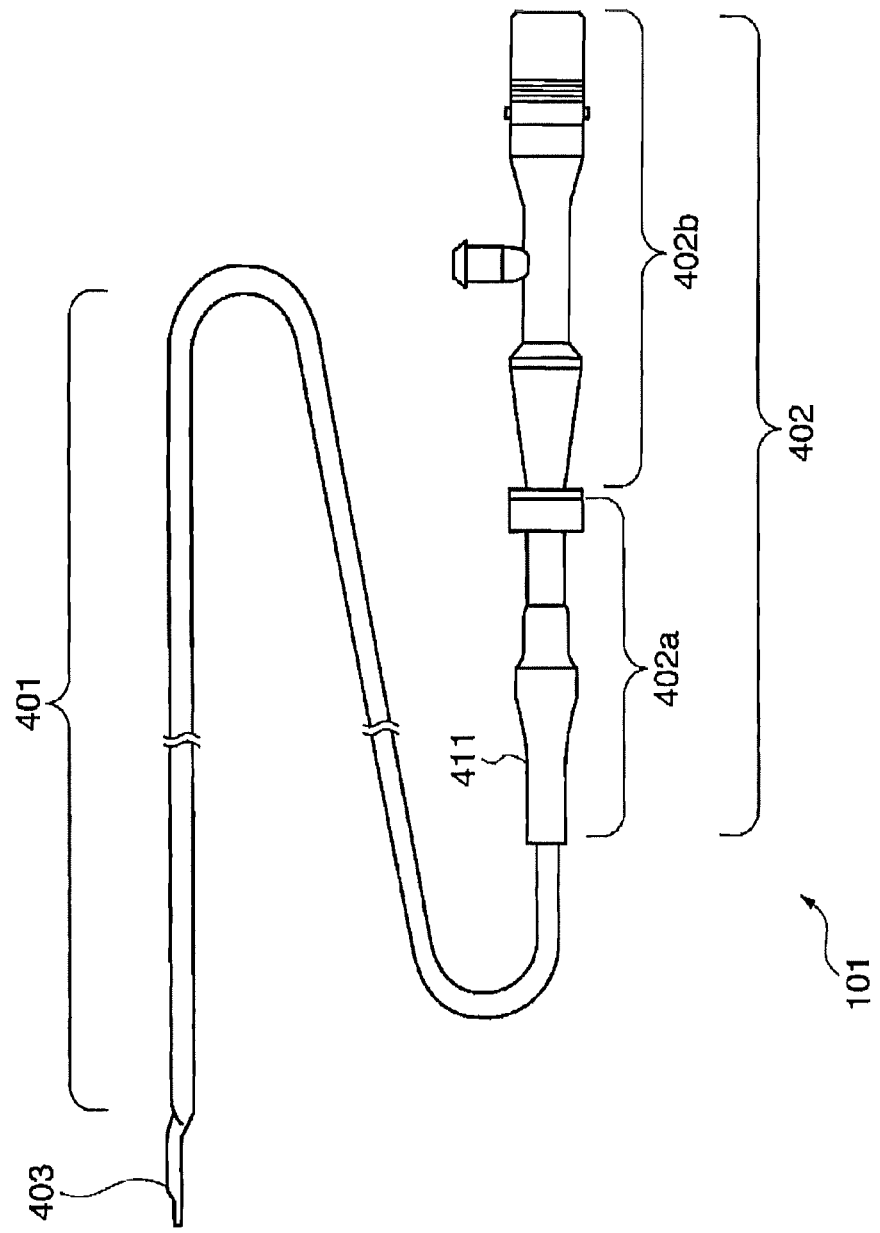
FIG. 4 is a perspective view of the outward appearance and constitution of an optical probe unit.

4. Construction of Optical Probe Unit
4.1 Overall Construction of Optical Probe Unit Set forth next, with reference to FIG. 4, is a description of the overall construction of the optical probe unit 101. As shown in FIG. 4, the optical probe unit 101 is constructed as an elongated catheter sheath 401 which is inserted into the blood vessel and a connector 402 which is arranged at the hand-side of a user without being inserted into the blood vessel in order to be steered by a user. At the distal end of the catheter sheath 401, there is formed a tube for guide wire lumen 403, and the catheter sheath 401 is formed as a continuous lumen from a connection portion with respect to the tube for guide wire lumen 403 over a connection portion with respect to the connector 402.

The connector 402 is composed of a sheath connector 402*a* constructed integrally at the proximal end of the catheter sheath 401 and a drive shaft connector 402*b* constructed integrally at the proximal end of a drive shaft.

At a boundary portion between the sheath connector 402*a* and the catheter sheath 401, an anti-kink protector 411 is provided. This helps maintain a predetermined rigidity, while also making it possible to inhibit or prevent bending (kinking) caused by a rapid change to a certain degree. The proximal end of the drive shaft connector 402*b* is constructed to be connectable with the scanner & pull-back unit 102.

4.2 Construction of Distal End Portion of Optical Probe Unit

Figure 5:
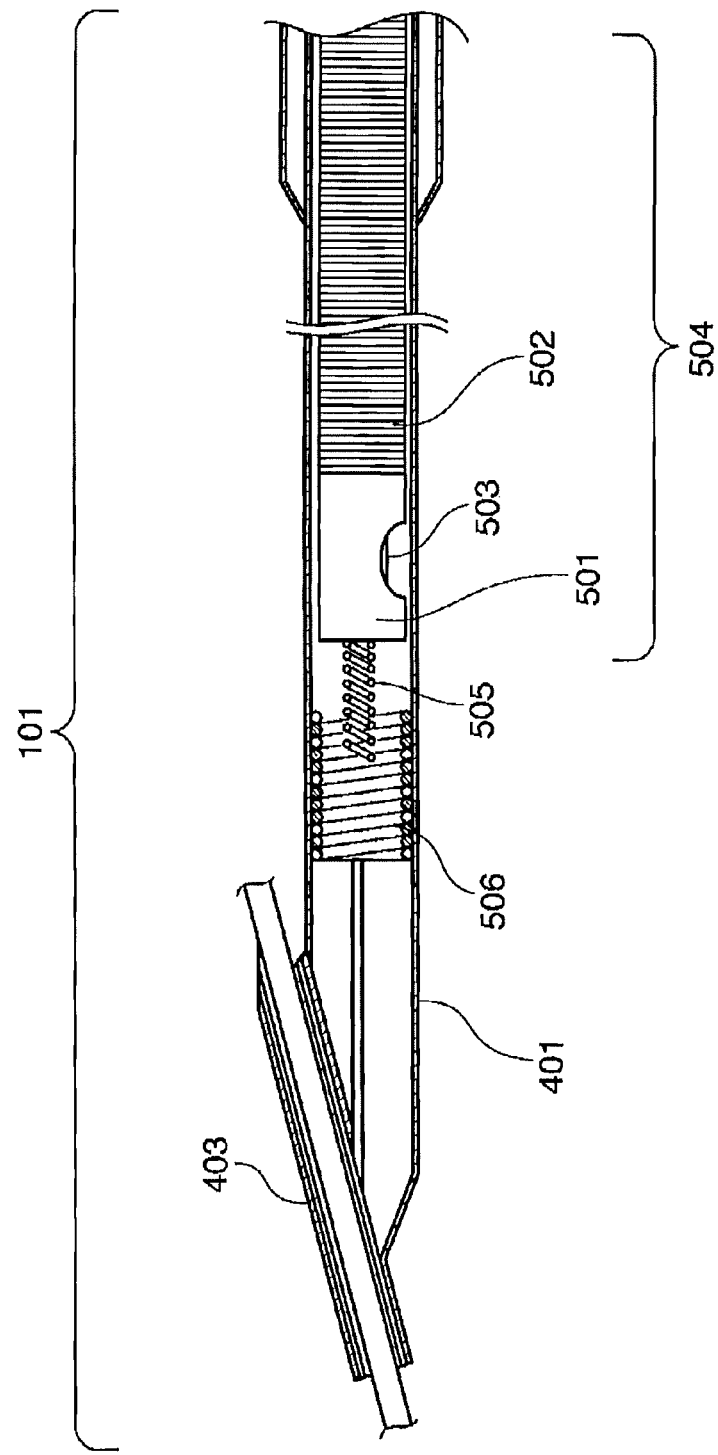
FIG. 5 is a longitudinal cross-sectional view of a distal end portion of the optical probe unit.

Referring to FIG. 5, set forth below is a description of distal end portion of the optical probe unit 101. As shown in FIG. 5, in the inside of the lumen of the catheter sheath 401, there are inserted an imaging core 504 (corresponding to reference numeral 201 in FIG. 2 and reference numeral 301 in FIG. 3) including a housing 501 in which a transmitting and receiving unit 503 for transmitting and receiving the measurement light is arranged and a drive shaft 502 for transmitting a drive force for rotating it approximately over full length thereof, and an optical probe unit 101 is formed thereby.

The transmitting and receiving unit 503 is installed with an optical mirror for laterally reflecting the measurement light transmitted by an optical fiber into which the drive shaft 502 is inserted so that the optical axis of the measurement light is laterally deflected.

In the transmitting and receiving unit 503, the measurement light is transmitted toward the tissue of the body cavity and concurrently, reflected light from the tissue of the body cavity is received.

The drive shaft 502 can be coil-shaped as illustrated and in the inside thereof, there is arranged a signal wire (single mode fiber).

The housing 501 forms a shape including a cut-out at a portion of a short cylindrical shaped metal pipe and it can be shaped/formed by cutting it out from a piece of metal, MIM (metal powder injection molding) or the like. The housing 501 includes the transmitting and receiving unit 503 in the inside, and the proximal end side of the housing is connected with the drive shaft 502. Also, there is provided on the distal end side with a short coil shaped flexible member 505.

The flexible member 505 is a member obtained by forming a stainless steel wire material in a coil shape and owing to a fact that the flexible member 505 is arranged on the distal end side, stability on an occasion of the rotation of the imaging core 504 is improved.

A reinforcing coil 506 helps prevent rapid bending of the distal end portion of the catheter sheath 401.

The tube for guide wire lumen 403 has a lumen for guide wire in which a guide wire is insertable. The tube for guide wire lumen 403 is used for accepting the guide wire inserted beforehand into the body cavity inside so that the guide wire can guide the catheter sheath 401 to the target lesion.

It is possible for the drive shaft 502 to perform rotational movement and axial movement with respect to the catheter sheath 401, and it is constructed, for example, by a multiple and multi-layered closely-attached coil or the like, composed of a metal wire of a stainless metal or the like, which is flexible and also has a characteristic in which rotation is well transmissible.

4.3 Cross-Sectional Construction of Imaging Core

Figure 6:
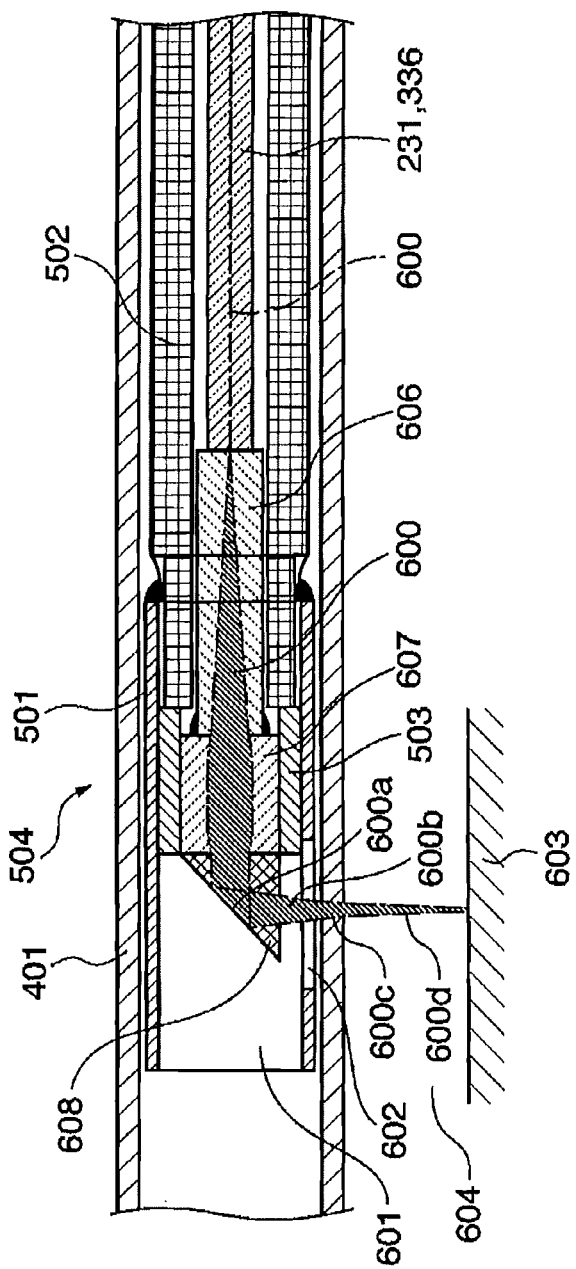
FIG. 6 is an enlarged longitudinal cross-sectional view of an imaging core.

FIG. 6 is a longitudinal cross-sectional view of the imaging core 504 of FIG. 5 showing the construction of the imaging core 504 and a light beam trajectory of the measurement light when an optical beam is transmitted. The fifth single mode fiber (optical fiber) 231, 336 is composed of a core which is a center portion whose refractive index is relatively high and a cladding or covering which exists at the periphery of the core and whose refractive index is relatively low, as much as 1% compared with that of the core. An optical beam 600 is transmitted while being totally-reflected at the boundary surface between the portions of the core and the cladding.

The optical beam reaching the distal end portion of the optical fiber 231, 336 is diffused inside a spacer 606 which is connected adjacently. The optical beam 600 diffused inside the spacer 606 is refracted inside a lens 607 which is connected to the spacer 606 adjacently and becomes a focused optical beam.

A focused optical beam 600a which is transmitted from the lens 607 is redirected approximately in the perpendicular direction by a mirror or prism 608. Then, the light is refracted at the boundary surface between the mirror or prism 608 and a medium (air) 601, and it becomes an optical beam 600b and passes through an aperture portion 602 of the housing 501.

Further, the optical beam 600b passed through the aperture portion 602 is refracted at the boundary surface (sheath inner surface) between the medium (air) 601 and the catheter sheath 401, and it becomes an optical beam 600c. Further, the optical beam 600c is refracted at the boundary surface (sheath outer surface) between the catheter sheath 401 and a medium (water) 604, it becomes an optical beam 600d, and after passing through the medium (water) 604, it is illuminated to a biological tissue 603 of a blood vessel or the like.

It should be noted that with respect to the optical beam 600 diffused inside the spacer 606, during a period until being illuminated to the biological tissue 603 of a blood vessel or the like, portions thereof are reflected on the lens 607 surface, on the sheath inner surface and on the sheath outer surface.

5. Operation Of Transmitting and Receiving Unit

Figure 7A:
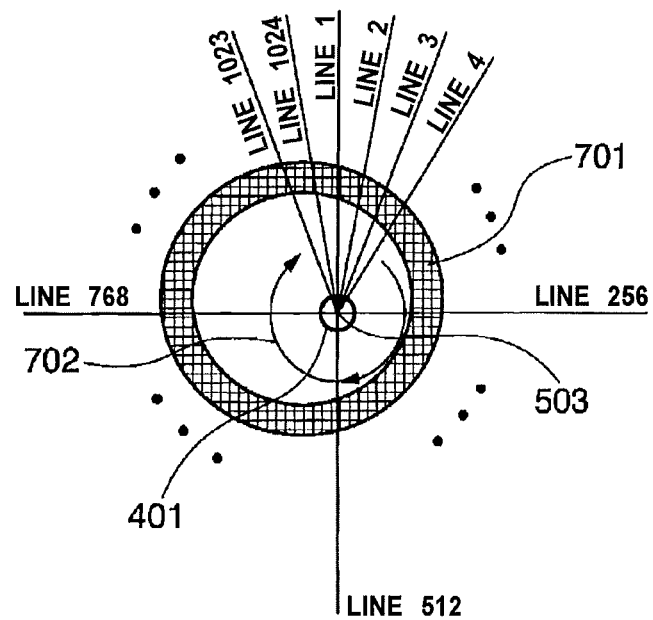
FIGS. 7A and 7B are diagrams schematically showing a cross-sectional image generated in a signal processing unit and a radial and longitudinal operation of a transmitting and receiving unit.
Figure 7B:
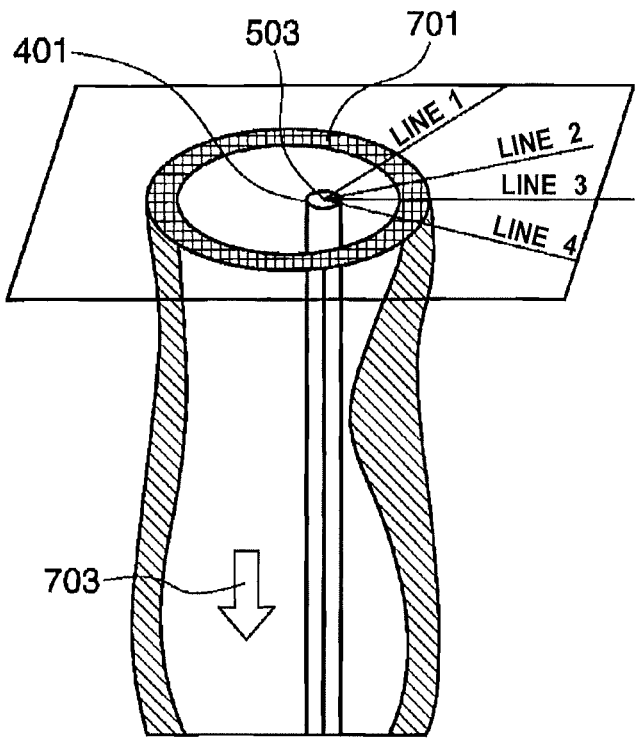

FIGS. 7A and 7B are schematic diagrams explaining operational aspects of the transmitting and receiving unit 503 at the time of the optical coherence tomographic image diagnosis. FIGS. 7A and 7B are a cross-sectional view and a prospective view respectively of a blood vessel respectively in a state in which the optical probe unit 101 is inserted in the blood vessel.

FIG. 7A illustrates the blood vessel 701 in cross-section, with the optical probe unit 101 inserted in the blood vessel. As mentioned above, the optical probe unit 101 is mounted with the transmitting and receiving unit 503 inside the distal end thereof and rotates in the direction of the arrow 702 through operation of the radial scanning motor 205, 305.

The transmission/reception of the measurement light is carried out at the transmitting and receiving unit 503 for respective rotary angles. Lines 1, 2, . . . 1024 show the transmitting directions of the measurement light in the respective rotary angles. In this embodiment disclosed by way of example, while the transmitting and receiving unit 503 is rotated 360 degrees in a predetermined blood vessel cross-section (701), the transmission/reception of the measurement light is carried out intermittently 1024 times. Of course, the apparatus and method are not limited in this regard as the number of transmissions/receptions of the measurement light during a period of rotating by 360 degrees is not limited to this number in particular and it is assumed to be settable as desired.

The transmission/reception of a measurement light is carried out while being advanced inside the blood vessel in the direction of the arrow 703 in FIG. 7B. A scan for repeating the transmission/reception of the measurement light in the respective blood vessel cross-sections in synchronization with the advance of the transmitting and receiving unit 503 in the arrow 703 direction is generally referred to as a "radial scan".

6. Line Data Used for Generation of Cross-Sectional Image

The description now turns to details of line data processed in the signal processing units 214, 323. The description which follows specifically pertains to line data processed in the signal processing unit 323 of the optical frequency domain imaging (OFDI) apparatus utilizing wavelength sweeping within the imaging apparatuses. It is to be understood that a similar configuration is employed also for the optical coherence tomography (OCT) apparatus and the associated signal processing unit 214. The signal processing units 214, 323 are examples of means for acquiring signals indicating an intensity distribution of the interference signal from a transmitting and receiving position of the light to a depth position inside the body cavity.

FIG. 8 is a diagram for explaining details of line data processed in the signal processing unit 323. In FIG. 8, the horizontal axis represents positional information and the vertical axis shows intensity (that is, FIG. 8 shows intensity distribution of the interference signal from a transmitting and receiving position to a certain depth position in a body cavity). The signal processing unit 323 (signal processing unit 214) is an obtaining unit that obtains signals generated every time the transmitting and receiving unit carries out transmission and reception of light and which indicate intensity distribution of the interference signal from the transmitting and receiving position of the light to a certain depth position inside the body cavity.

As shown in FIG. 8, it is possible to roughly classify the line data generated based on the interference signal obtained by the transmission and reception of the measurement light depending on the transmitting and receiving unit 503 shown in FIG. 6 into a signal from the catheter sheath 401 inside and a signal which is from the catheter sheath 401 outside and which includes information used for diagnosis.

In the signal from the catheter sheath 401 inside, there are further included 1) a signal based on light reflected at the lens surface, 2) a signal based on light reflected at the sheath inner surface and 3) a signal based on light reflected at the sheath outer surface.

In the case of the imaging apparatus 100, when an abnormality occurs in the optical probe unit 101, changes occur in the line data. The apparatus disclosed here is constructed to utilize the line date (changes in the line data) to detect an abnormality occurring in the optical probe unit 101. In the disclosed embodiment described by way of example, the monitoring unit 338 of the imaging apparatus 100 is constructed to detect an abnormality occurring in the optical probe unit 101 based on the changes occurring or observed in the line data.

7. Change of Line Data and Estimated Situation

Set forth next is an explanation of the relationship between the occurrence of an abnormality in the optical probe unit 101 and changes in the line data.

In a case in which the transmitting and receiving unit 503 is highly curved or bent, the following changes occur in the line data compared with a normal state thereof.

1) Intensity of the signal from the lens surface decreases or the position (coordinate) at which the signal appears moves.
2) Intensity of the signal from the sheath inner surface decreases or the position (coordinate) at which the signal appears moves.
3) Intensity of the signal from the sheath outer surface decreases or the position (coordinate) at which the signal appears moves.

In a case in which all changes 1) to 3) described above occur, the signal processing unit 323 judges or determines that an abnormality occurred in the optical probe unit 101. Whether or not the changes occur is determined based on the comparison of the above factors or values with the respective thresholds set based on the signal intensity from the lens surface and the coordinates thereof; the signal intensity from the sheath inner surface and the coordinates thereof; and the signal intensity from the sheath outer surface and the coordinates thereof, all of which are obtained at the time of calibration held beforehand.

Also, in a case in which a kink of the catheter sheath 401 or a cut-off of the transmitting and receiving unit 503 occurs, the following changes occur in the line data compared with a normal state thereof.
1) Intensity of the signal from the lens surface decreases.
2) Intensity of the signal from the sheath inner surface decreases.
3) Intensity of the signal from the sheath outer surface decreases.
4) Intensity of the signal from the catheter sheath 401 outside decreases or increases.

In a case in which all changes of 1) to 4) described above occur, the signal processing unit 323 judges or determines that an abnormality has occurred in the optical probe unit 101. Whether or not the changes have occurred is determined or judged by comparing the above factors or values with respective thresholds set based on the signal intensity from the lens surface, the signal intensity from the sheath inner surface, the signal intensity from the sheath outer surface, and the signal intensity from the catheter sheath outside, all of which are obtained at the time of calibration held beforehand.

Also, in a case in which the transmitting and receiving unit 503 becomes stuck during the pull-back, the following changes occur in the line data compared with a normal state thereof.
1) Position (coordinate) at which the signal from the lens surface appears moves.
2) Position (coordinate) at which the signal from the sheath inner surface appears moves.
3) Position (coordinate) at which the signal from the sheath outer surface appears moves.

In a case in which all changes 1) to 3) described above occurred, the signal processing unit 323 judges or determines that an abnormality has occurred in the optical probe unit 101. Whether or not the changes have occurred is determined or judged by comparing the above factors or values with thresholds set based on the coordinate of the signal from the lens surface, the coordinate of the signal from the sheath inner surface, and the coordinate of the signal from the sheath outer surface, all of which are obtained at the time of calibration held beforehand.

Also, in a case in which the blood intrudes inside the catheter sheath 401, the following changes occur in the line data compared with a normal state thereof.
1) Intensity of the signal from the sheath inner surface decreases.
2) Intensity of the signal from the sheath outer surface decreases.
3) Intensity of the signal from the sheath outside decreases.

In a case in which all changes 1) to 3) described above occur, the signal processing unit 323 judges or determines that an abnormality occurred in the optical probe unit 101. Whether or not the changes have occurred is determined or judged by comparing the above factors or values with thresholds set based on the signal intensity from the sheath inner surface, the signal intensity from the sheath outer surface, and the signal intensity from the catheter sheath outside, all of which are obtained at the time of calibration held beforehand.

Further, in a case in which the transmitting and receiving unit 503 vibrates, the following changes occur in the line data compared with a normal state thereof.
1) Position (coordinate) at which the signal from the lens surface appears fluctuates.
2) Position (coordinate) at which the signal from the sheath inner surface appears fluctuates.
3) Position (coordinate) at which the signal from the sheath outer surface appears fluctuates.

In a case in which all changes 1) to 3) described above occurred, the signal processing unit 323 judges or determines that an abnormality occurred in the optical probe unit 101. Whether or not the changes have occurred is determined or judged by comparing differential values calculated at the coordinates of the respective signals with the preset thresholds calculated based on a differential value of the coordinate of the signal from the lens surface, a differential value of the coordinate of the signal from the sheath inner surface, and a differential value of the coordinate of the signal from the sheath outer surface.

8. One Example of Line Data in a Normal Case and Line Data in an Abnormal Case

The following description explains examples of line data in a normal case and line data in an abnormal case based on line data which is generated actually. FIGS. 9A-1, 9A-2, 9B-1 and 9B-2 are diagrams showing one example of line data in a normal case and line data in an abnormal case. FIG. 9A-2 is a diagram showing one example of line data in a normal case and FIG. 9A-1 is a view showing one example of a cross-sectional image which is generated using the line data of FIG. 9A-2.

The horizontal axis in FIG. 9A-2 represents positional information and the vertical axis represents intensity. Also, reference numeral 901 indicates a signal from the lens surface, reference numeral 902 indicates a signal from the sheath inner surface and reference numeral 903 indicates a signal from the sheath outer surface, respectively.

FIG. 9B-2 is a diagram showing one example of line data in a case in which the transmitting and receiving unit 503 is highly curved and FIG. 9B-1 is a view showing one example of a cross-sectional image generated by using the line data of FIG. 9B-2.

The horizontal axis in FIG. 9B-2 represents positional information and the vertical axis represents intensity. Also, reference numeral 911 indicates a signal from the lens surface, reference numeral 912 indicates a signal from the sheath inner surface and reference numeral 913 indicates a signal from the sheath outer surface.

As is clear from a comparison of FIG. 9A-2 with FIG. 9B-2, in a case in which the transmitting and receiving unit 503 is relatively highly curved, the position (coordinate) at which the signal from the lens surface appears is moved (921), the signal intensity from the sheath inner surface decreases (922), and the position (coordinate) at which the signal from the sheath outer surface appears is moved (923).

9. Details of Safety Monitoring Process in Safety Monitoring Unit 338

Figure 10:
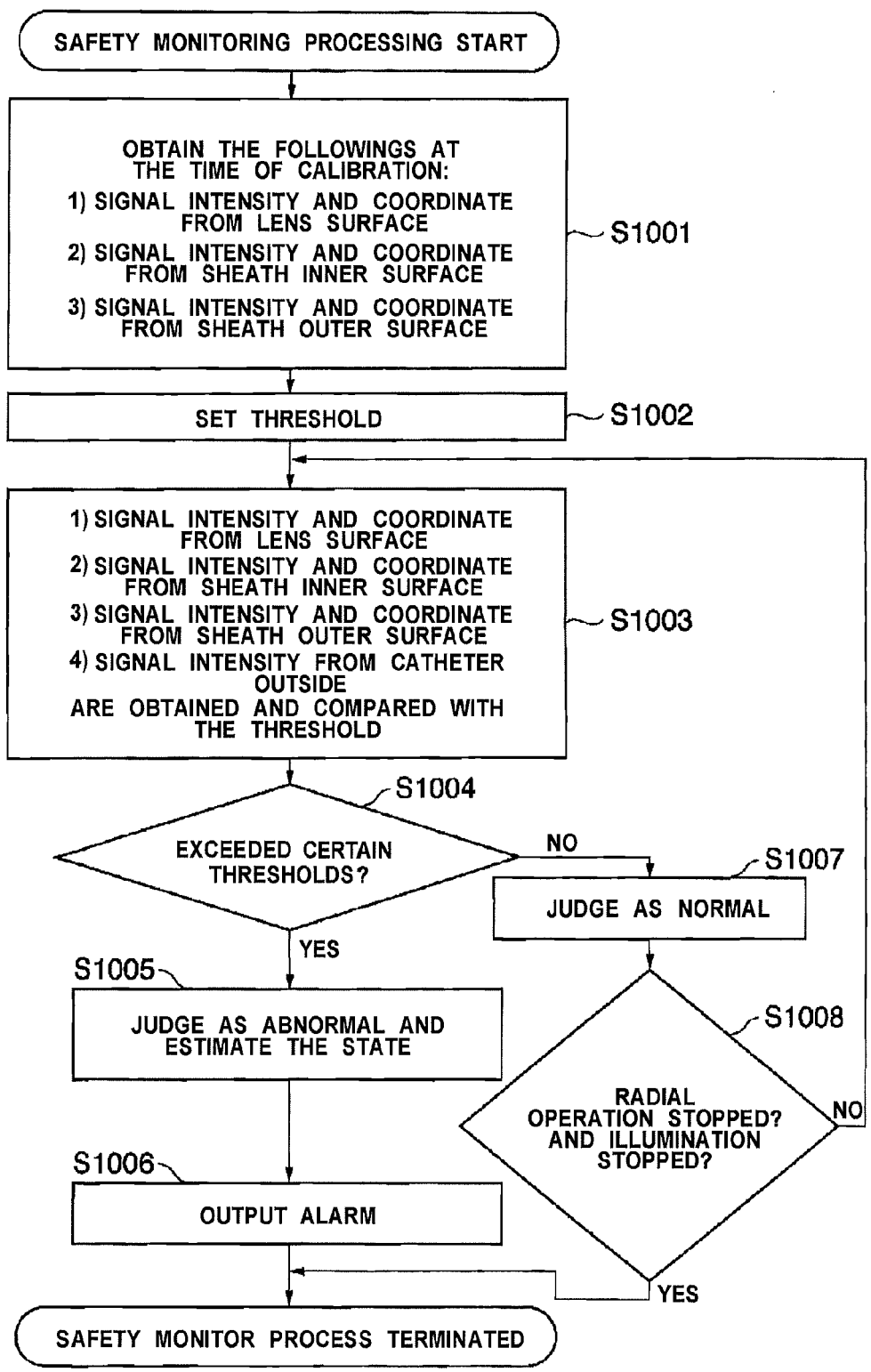
FIG. 10 is a flowchart showing a flow of a monitoring process or safety monitoring process performed in the signal processing unit.

The following description explains a safety monitoring process in the safety monitoring unit 338 of the signal processing unit 323. FIG. 10 illustrates an example of a flowchart of a safety monitoring process performed by the safety monitoring unit 338 of the signal processing unit 323. The monitoring unit 323 (monitoring unit 233) is a judgment unit that judges whether or not the optical probe unit 101 is normal (abnormal) based on the existence or non-existence of intensity change in at least a portion of the signals obtained by the signal processing unit 323 (214), based on the existence or non-existence of change of position in the depth direction in which the portion of signals appear, or based on change quantity per unit time with respect to the position in which the portion of signals appear.

When the radial scanning operation is started by the scanner & pull-back unit 102 or when the illumination of the measurement light is started by the wavelength swept light source 308, the monitoring start process or safety start process shown in FIG. 10 is performed.

In step S1001, the monitoring unit 338 reads-in 1) the signal intensity and the coordinate of the signal intensity from the lens surface, 2) the signal intensity and the coordinate of the signal intensity from the sheath inner surface and 3) the signal intensity and the coordinate of the signal intensity from the sheath outer surface, all of which are obtained and stored inside the signal processing unit 323 beforehand at the time of calibration.

In step S1002, based on the respective signal intensities and the coordinates of the signal intensities which are read in at step S1001, respectively set are the thresholds for judging whether or not the signal intensities decrease and the thresholds for judging whether or not the coordinates of the signals change. Also, the threshold for judging whether or not the coordinates of the signals fluctuate is set in the same manner.

Further, thresholds (assumed to be predetermined at the time of calibration) for judging whether or not the signal intensity from the outside of the catheter sheath 401 decreases or increases is set.

In step S1003, with respect to the line data generated in the signal processing unit 323, there are obtained 1) signal intensity and coordinate from the lens surface, 2) signal intensity and coordinate from the sheath inner surface, 3) signal intensity and coordinate from the sheath outer surface and 4) signal intensity from the outside of the catheter sheath. These values are compared with the thresholds set in step S1002.

In step S1004, in response to the result of the comparison in step S1003, it is judged whether or not certain thresholds are exceeded. In case it is judged in step S1004 that the threshold is exceeded, the process proceeds to step S1005, and it is judged that abnormality occurred in the optical probe unit 101 and the cause of the abnormality which occurred in the optical probe unit 101 is estimated. The process flow moves from step S1004 to step S1005 when certain (all or part of) the thresholds are exceeded.

In step S1006, an alarm with respect to the cause of abnormality which was estimated in step S1005 is outputted. That is, the system notifies the user about the abnormality that has been estimated.

When it is judged or determined in step S1004 that the threshold is not exceeded, the process proceeds to step S1007 and it is judged or determined that the optical probe unit 101 is normal. Further, in step S1008, it is judged or determined whether or not the radial scanning operation is continued by the scanner & pull-back unit 102 and whether or not the illumination of the measurement light depending on the wavelength swept light source 308 is continued.

When it is judged or determined in step S1008 that the radial scanning and illumination are continuing, the process returns to step S1003 and the monitoring process continues.

When it is determined or judged in step S1008 that the radial scanning and/or the illumination is not continuing, the monitoring process (safety monitoring process) is terminated. That is, the security monitoring process is terminated when the radial scanning or the illumination no longer continues.

The imaging apparatus in this embodiment described by way of example is constructed so that the existence or non-existence of the occurrence of abnormality in the optical probe unit 101 is judged based on the existence or non-existence of the change of the intensity of at least a portion of a signal included in the line data processed in the signal processing unit, based on the existence or non-existence of the change of the position at which the signal appears and based on the change quantity per unit time of the position in which the signal appears, and so that a notice is sent to the user in case of judging that the abnormality occurred. The notice can be displayed on the display 113, 215, 317 so that the displays operate as a notice unit that provides notification of the judgment about whether an abnormality has occurred or been detected. The monitoring unit 338 (233) carrying out the process flow shown by way of example in FIG. 10 is an example of a determining means for determining that the optical probe unit is abnormal: i) when there exists a change in the intensity of at least a portion of the signals acquired by the means for acquiring; ii) when there exists a change of position in a depth direction in which the portion of signals appear; or iii) based on change quantity per unit time with respect to the position in which the portion of signals appear.

Thus, it becomes possible for the user to recognize the abnormality which occurs in the optical probe unit 101 rather quickly.

Also, in the imaging apparatus described above by way of example, when an abnormality is found to have occurred, the apparatus and method estimate the cause of the abnormality occurrence, and the user is so notified.

Thus, it becomes possible for the user to recognize the cause of the abnormality relatively quickly and it becomes possible to take proper measures (e.g., stopping the scan operation, stopping the pull-back operation, stopping the illumination of the measurement light, etc.) in response to the cause of the abnormality.

As a result, it becomes possible to avoid injuring a patient and perform visualization of the cross-sectional image more safely.

[Second Embodiment]

The first embodiment of the apparatus and method described above by way of example employ a construction in which an alarm is outputted when it is determined or judged that an abnormality has occurred, but the apparatus and method are not limited in this regard. It is also possible, for example, to employ a construction in which in response to the cause of the estimated abnormality, the appropriate operation is stopped, for example the scan operation is stopped automatically, the pull-back operation is stopped automatically or the illumination of the measurement light is stopped automatically. In this regard, the motor control circuits 225, 324 can operate as a controller for: i) controlling the rotary operation of the transmitting and receiving unit to stop when the judgment unit determines or judges that the optical probe unit is not normal; ii) controlling the pull-back operation or operation in the longitudinal direction of the transmitting and receiving unit when the judgment unit determines or judges that the optical probe unit is not normal; and iii) controlling the light transmission and reception or light illumination of the transmitting and receiving unit when the judgment unit determines or judges that the optical probe unit is not normal.

The first embodiment described above also employs a construction in which an abnormality is judged or determined when a plurality of changes occur, but the apparatus and method here are not limited in this regard. It is also possible to employ a construction in which an abnormality is determined or judged by focusing on any one of or a portion of the changes.

The detailed description above describes features and aspects of embodiments of an imaging apparatus and a control method which are disclosed by way of example. The invention is not limited, however, to the precise embodiments and variations described. Various changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. An imaging apparatus comprising:
an optical probe unit positionable in a body cavity and comprising a transmitting and receiving unit configured to transmit light and to receive reflected light which has reflected from within the body cavity as the transmitting and receiving unit rotates and moves longitudinally in the body cavity, with a cross-sectional image of the body cavity being generated based on an interference signal generated using the received reflected light, the transmitting and receiving unit being positioned in a catheter sheath which possesses a sheath inner surface and a sheath outer surface, the transmitting and receiving unit including a lens from which the light is transmitted, the lens possessing a lens surface;
an obtaining unit which obtains intensity distribution signals indicating an intensity distribution of the interference signal from a transmitting and receiving position of the light to a depth position inside the body cavity, the intensity distribution signals obtained by the obtaining unit including a first signal constituting light reflected from the lens surface, a second signal constituting light reflected from the sheath inner surface, and a third signal constituting light reflected from the sheath outer surface; and
determining means for determining that the optical probe unit is abnormal: i) when there exist respective changes in intensity, which are greater than respective predetermined changes in intensity, of at least respective portions of the first, second and third signals acquired by the obtaining unit;
ii) when there exist respective changes of position in a depth direction, which are greater than respective predetermined changes of position in the depth direction, in which the respective portions of the first, second and third signals appear; or iii) based on respective change quantities per unit time with respect to position, which are greater than respective predetermined change quantities per unit time with respect to position, in which the respective portions of the first, second and third signals appear, and for determining the cause of abnormality of the optical probe unit.

2. The imaging apparatus according to claim 1, wherein the determining means determines the abnormality of the optical probe when the intensity of at least a portion of the first, second and third signals decreases.

3. An imaging apparatus comprising:
an optical probe unit positionable in a body cavity and comprising a transmitting and receiving unit configured to transmit light and to receive reflected light which has reflected from the body cavity during longitudinal and rotational movement of the transmitting and receiving unit inside the body cavity, with a cross-sectional image in a longitudinal direction of the body cavity being generated based on an interference signal generated by the received reflected light, the transmitting and receiving unit including a sheath covering a lens from which the light is transmitted, the sheath possessing a sheath inner surface and a sheath outer surface, the lens possessing a lens surface;
an obtaining unit which obtains intensity distribution signals which are generated every time when the transmitting and receiving unit carries out transmission and reception of light and which indicate intensity distribution of the interference signal from a transmitting and receiving position of the light to a certain depth position inside the body cavity, the intensity distribution signals obtained by the obtaining unit including a first signal constituting light reflected from the lens surface, a second signal constituting light reflected from the sheath inner surface, and a third signal constituting light reflected from the sheath outer surface; and
a judgment unit which judges, while the optical probe unit is positioned in the body cavity, whether or not the optical probe unit is normal based on existence or non-existence of respective intensity changes, which are greater than respective predetermined intensity changes, in at least respective portions of the first, second and third signals obtained by the obtaining unit, based on existence or non-existence of respective changes of position in the depth direction, which are greater than respective predetermined changes of position in the depth direction, in which the respective portions of the first, second and third signals appear, or based on respective change quantities per unit time with respect to position, which are greater than respective predetermined change quantities per unit time with respect to position, in which the respective portions of the first, second and third signals appear.

4. The imaging apparatus according to claim 3, wherein the judgment unit judges that the optical probe unit is abnormal when an intensity of at least a portion of the first, second and third signals decreases.

5. The imaging apparatus according to claim 3, further comprising a notice unit which provides notice that the judgment unit has judged the optical probe unit to be abnormal.

6. A control method in an imaging apparatus comprised of an optical probe unit positionable in a body cavity and comprising a transmitting and receiving unit which carries out transmission and reception of light continuously, with reflected light from the body cavity being received at the transmitting and receiving unit during rotational and longitudinal movement of the transmitting and receiving unit inside the body cavity so that a cross-sectional image in a longitudinal direction of the body cavity is generated based on interference signal generated by the received reflected light, the transmitting and receiving unit including a lens positioned inside a sheath, the sheath possessing a sheath inner surface and a sheath outer surface, the lens possessing a lens surface, the method comprising:
obtaining intensity distribution signals generated when the transmitting and receiving unit carries out transmission and reception of light and which indicate intensity distribution of an interference signal from a transmitting and receiving position of the light to a certain depth position inside the body cavity, the obtained intensity distribution signals including a first signal constituting light reflected from the lens surface, a second signal constituting light reflected from the sheath inner surface, and a third signal constituting light reflected from the sheath outer surface; and
judging whether or not the optical probe unit is normal based on existence or non-existence of respective intensity changes, which are greater than respective predetermined intensity changes, in all of the respective first, second and third signals, based on existence or non-existence of respective changes of position in a depth direction, which are greater than respective predetermined changes of position in the depth direction, in which all of the respective first, second and third signals appear, or based on respective change quantities per unit time with respect to position in the depth direction, which are greater than respective predetermined change quantities per unit time with respect to position in the depth direction, in which all of the respective first, second and third signals appear.

7. The control method according to claim 6, wherein the judging further comprises judging that the optical probe unit is abnormal when the intensity of at least a portion of the first, second and third signals decreases.

* * * * *